(12) United States Patent
Young

(10) Patent No.: US 12,193,926 B2
(45) Date of Patent: *Jan. 14, 2025

(54) SIZE ADJUSTABLE DEVICE TO COVER AND SECURE IMPLANTABLE DEVICES IN SURGICAL APPLICATIONS

(71) Applicant: Ott Solutions, Cheyenne, WY (US)

(72) Inventor: Anke Young, New Canaan, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 18/129,950

(22) Filed: Apr. 3, 2023

(65) Prior Publication Data
US 2023/0233308 A1    Jul. 27, 2023

Related U.S. Application Data

(63) Continuation of application No. 17/367,743, filed on Jul. 6, 2021, now Pat. No. 11,642,207, which is a
(Continued)

(51) Int. Cl.
*A61F 2/12* (2006.01)
*A61F 2/00* (2006.01)
(Continued)

(52) U.S. Cl.
CPC .......... *A61F 2/0077* (2013.01); *A61L 27/362* (2013.01); *A61L 27/54* (2013.01);
(Continued)

(58) Field of Classification Search
CPC ........ A61F 2/0063; A61F 2/12; A61F 2/0077; A61F 2/52; A61L 27/362; A61L 27/38; A61L 27/54; A61B 17/0401
See application file for complete search history.

(56) References Cited

U.S. PATENT DOCUMENTS

| 2002/0188317 A1 | 12/2002 | Rousseau |
| 2015/0223928 A1 | 8/2015 | Limem et al. |
| 2020/0405473 A1 | 12/2020 | Nanni |

FOREIGN PATENT DOCUMENTS

| WO | WO2019175911 | 9/2019 | |
| WO | WO-2019175911 A2 * | 9/2019 | ........... A61F 2/0077 |

OTHER PUBLICATIONS

European Search Report And European Search Opinion for PCT/US2021/031117 established by the EPO completed on Oct. 28, 2024.

* cited by examiner

*Primary Examiner* — Brian A Dukert
*Assistant Examiner* — Rebecca Lynee Zimmerman
(74) *Attorney, Agent, or Firm* — Goldstein Law Offices, P.C.

(57) ABSTRACT

A size adjustable cover used for soft tissue reinforcement which is adapted to envelop an implantable device, such as a breast implant, in a surgical application. The cover is formed using a circular two-dimensional implantable matrix material having an inner circle and a plurality of fringes which radiate circumferentially from the inner circle. The implantable device is positioned upon the inner circle, and the plurality of fringes are folded inwardly to form an overlapping implant pocket which envelops the implantable device. Each fringe further has a punched opening, allowing a loop of suture thread to link each fringe together. Certain fringes are excluded from the loop to create stabilization tabs which radiate from the inner circle and are attached to a site of host implantation to stabilize the cover and the implantable device within.

13 Claims, 14 Drawing Sheets

Related U.S. Application Data continuation of application No. 16/515,142, filed on Jul. 18, 2019, now Pat. No. 11,090,146.

(60) Provisional application No. 62/809,135, filed on Feb. 22, 2019.

(51) Int. Cl.
  *A61L 27/36* (2006.01)
  *A61L 27/54* (2006.01)
  *A61B 17/04* (2006.01)
  *A61L 27/38* (2006.01)

(52) U.S. Cl.
  CPC ......... *A61B 17/0401* (2013.01); *A61F 2/0063* (2013.01); *A61F 2/12* (2013.01); *A61L 27/38* (2013.01)

SIZE ADJUSTABLE DEVICE TO COVER AND SECURE IMPLANTABLE DEVICES IN SURGICAL APPLICATIONS

CROSS-REFERENCE TO RELATED APPLICATIONS

This is a continuation of U.S. nonprovisional patent application Ser. No. 17/367,743, filed Jul. 6, 2021, which is a continuation of U.S. nonprovisional patent application Ser. No. 16/515,142 (now issued U.S. Pat. No. 11,090,146), filed Jul. 18, 2019, which claims priority to U.S. provisional patent application No. 62/809,135, filed Feb. 22, 2019. The foregoing applications are each herein incorporated by reference in their entirety.

TECHNICAL FIELD

The present disclosure relates generally to a device for preparing implantable devices for use in surgical applications. More particularly, the present disclosure relates to a size adjustable dermal matrix cover for enveloping an implantable device prior to implantation.

BACKGROUND

Implantable devices, such as breast implants and tissue expanders, require coverage with host tissue at the site of implantation, or coverage with a dermal or synthetic skin tissue matrix. Implantable devices also require stabilization at the site of host implantation to prevent the devices from shifting after implantation. Implantable devices cannot be sewn directly to host tissue without damage to the shell of the implantable device. Therefore, stabilization is often achieved by encasing the implantable device with implantable matrix material, such as acellular dermal matrixes, or by elevating host muscle and fascia. However, elevation of host fascia and muscle causes significant pain and disability in patients.

Acellular dermal matrixes are currently being used to both cover and stabilize breast implants or tissue expanders on the patient's chest wall by sewing multiple strips of usually square, rectangular or oval shaped devices to each other and then to the chest wall surrounding the implant or tissue expander. This practice of using multiple strips of dermal matrix has several important disadvantages. First, this practice results in significant wastage of expensive matrix material, and leads to increased preparation time within the operating room. Secondly, joining the different pieces of matrix results in palpable suture lines in the finished reconstruction. These suture lines may trigger false alarms in the future, leading to unnecessary imaging, tests, and biopsies.

There is also a possibility of lateral chest wall nerve entrapment. A suture line on the lateral aspect of the implant enclosure is necessary to prevent implant migration into the axillary area. However, a suture line which inadvertently runs across nerves which are superficial and abundant in this area, can lead to acute as well as chronic pain. In addition, changes in the dimensions of the implant pocket secondary to loosening of chest wall sutures can lead to implant malposition over time, resulting in revision surgeries for repositioning the implant.

Furthermore, this practice increases the risk of a needle puncture of the implantable device occurring during suture stabilization of the dermal matrix sheets to the chest wall. A needle puncture can lead to a rupture of the implantable device, requiring an otherwise avoidable surgical procedure to replace the damaged implantable device.

Finally, implantable devices vary widely in shape and size. For example, the implantable devices used in breast surgery are spherical or conical. Thus the practice of covering implantable devices using a patchwork of multiple pieces of dermal matrix continues, as it would be cost prohibitive to produce matrix covers uniquely configured to cover each type of implantable device.

Clearly, there is a need for an improved implantable matrix cover suitable for encasing implantable devices with varying dimensions, which addresses the problem of palpable suture lines causing nerve entrapment, and further avoids the use of stabilization methods which can cause needle punctures in the implantable device.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to provide a cover formed from a single piece of two-dimensional implantable matrix material with minimal wastage, which is capable of encasing an implantable device for use in a surgical procedure. Accordingly, the present disclosure provides a circular cover formed of implantable matrix material having an outer circle and a concentric inner circle. The outer circle is formed from a plurality of fringes which radiate circumferentially from the inner circle. The implantable device is placed upon the inner circle, while the fringes fold inwardly to form an overlapping implant pocket which fully envelops or encases the implantable device.

It is another aspect of an example embodiment in the present disclosure to provide a cover which can be stabilized at a site of host implantation without risk of puncturing the implantable device. Accordingly, the present disclosure provides a cover having a plurality of integral stabilization tabs which radiate from the inner circle after the overlapping implant pocket is formed, allowing the cover and the implanted device to be stabilized and centered at the site of host implantation via the stabilization tabs.

It is yet another aspect of an example embodiment in the present disclosure to provide a cover which envelops the implantable device without creating palpable suture lines which appear on medical imaging or which can entrap nerves. Accordingly, the present disclosure provides a cover with a punched opening on each of the plurality of fringes, allowing a loop of suture thread to be threaded circumferentially through each fringe while the cover lies flat and open, whereby the loop is tightened to pull the fringes inwardly to envelop the implantable device and form the overlapping implant pocket.

It is a further aspect of an example embodiment in the present disclosure to provide a cover which can be adjusted to the dimensions of the implantable device. Accordingly, the present disclosure provides a cover with fringes having fringe tips which can be trimmed in length to adjust for the diameter of the implantable device.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 1:
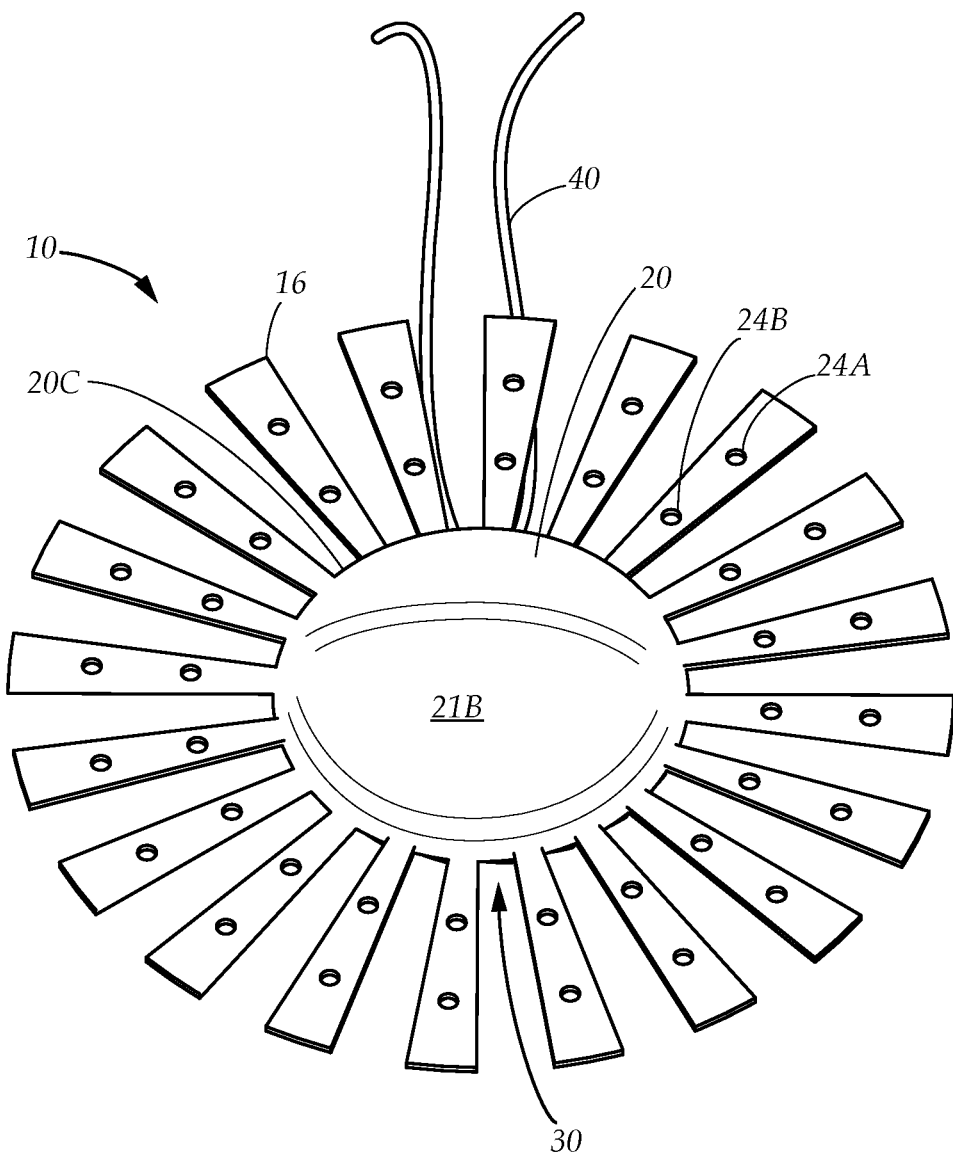
FIG. 1 is a diagrammatic perspective view of a size adjustable cover formed of an implantable matrix material, such as acellular dermal matrix, in accordance with an embodiment in the present disclosure.
Figure 2:
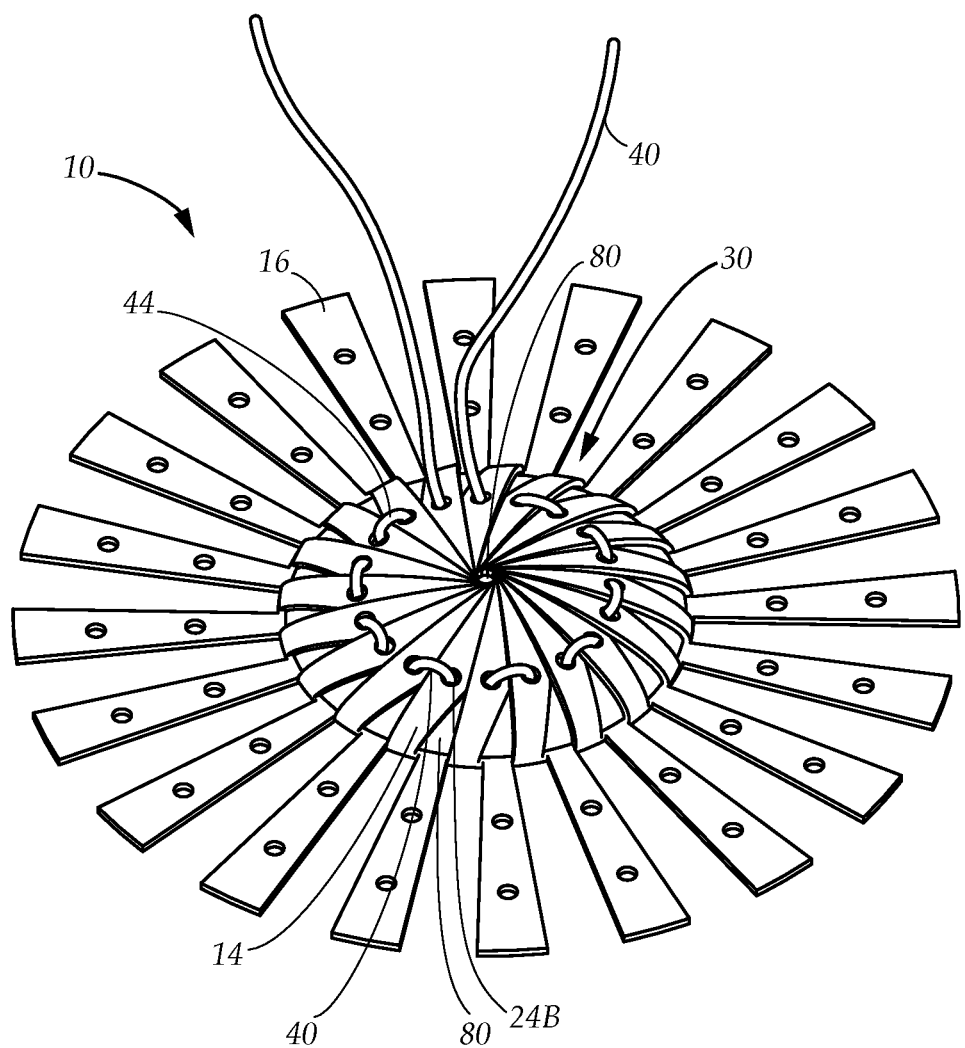
FIG. 2 is a diagrammatic perspective view of the size adjustable cover, showing an overlapping implant pocket formed from a plurality of radially projecting fringes, in accordance with an embodiment in the present disclosure.
Figure 3:
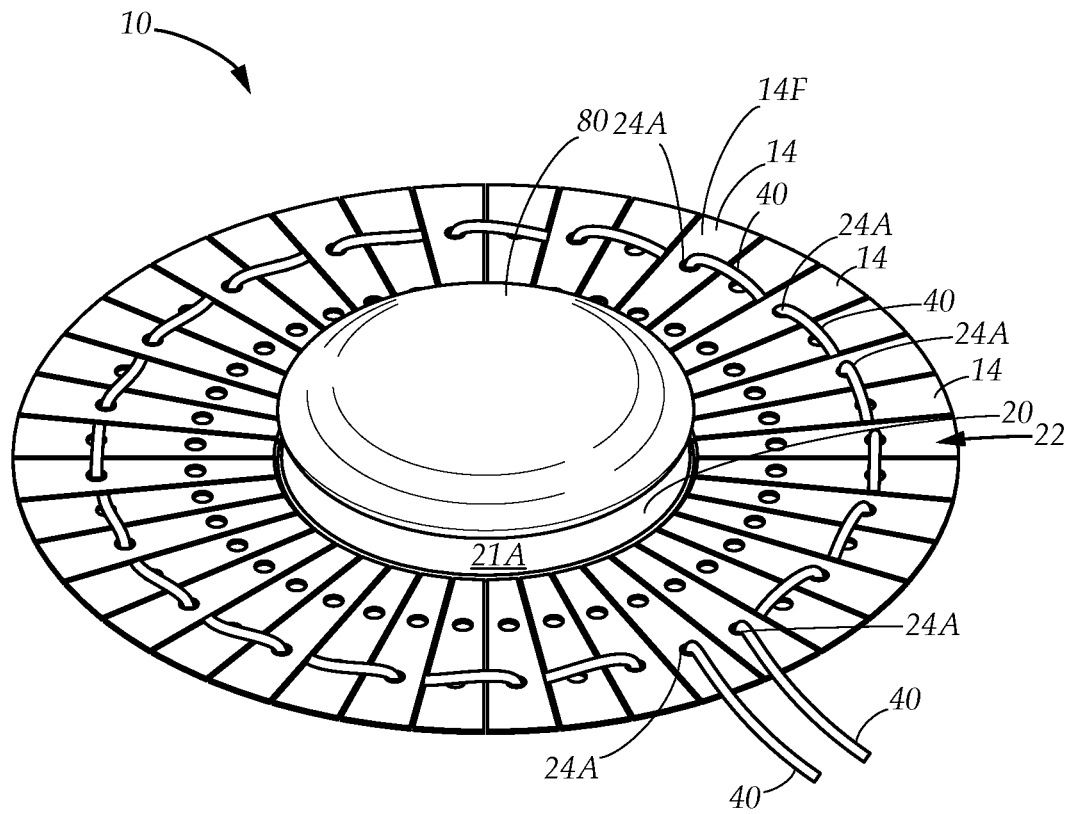
FIG. 3 is a diagrammatic perspective view of the size adjustable cover, depicting an inner circle from which the fringes radiate, and an outer circle formed by the fringes, further showing an implantable device positioned upon the inner circle, in accordance with an embodiment in the present disclosure.
Figure 14:
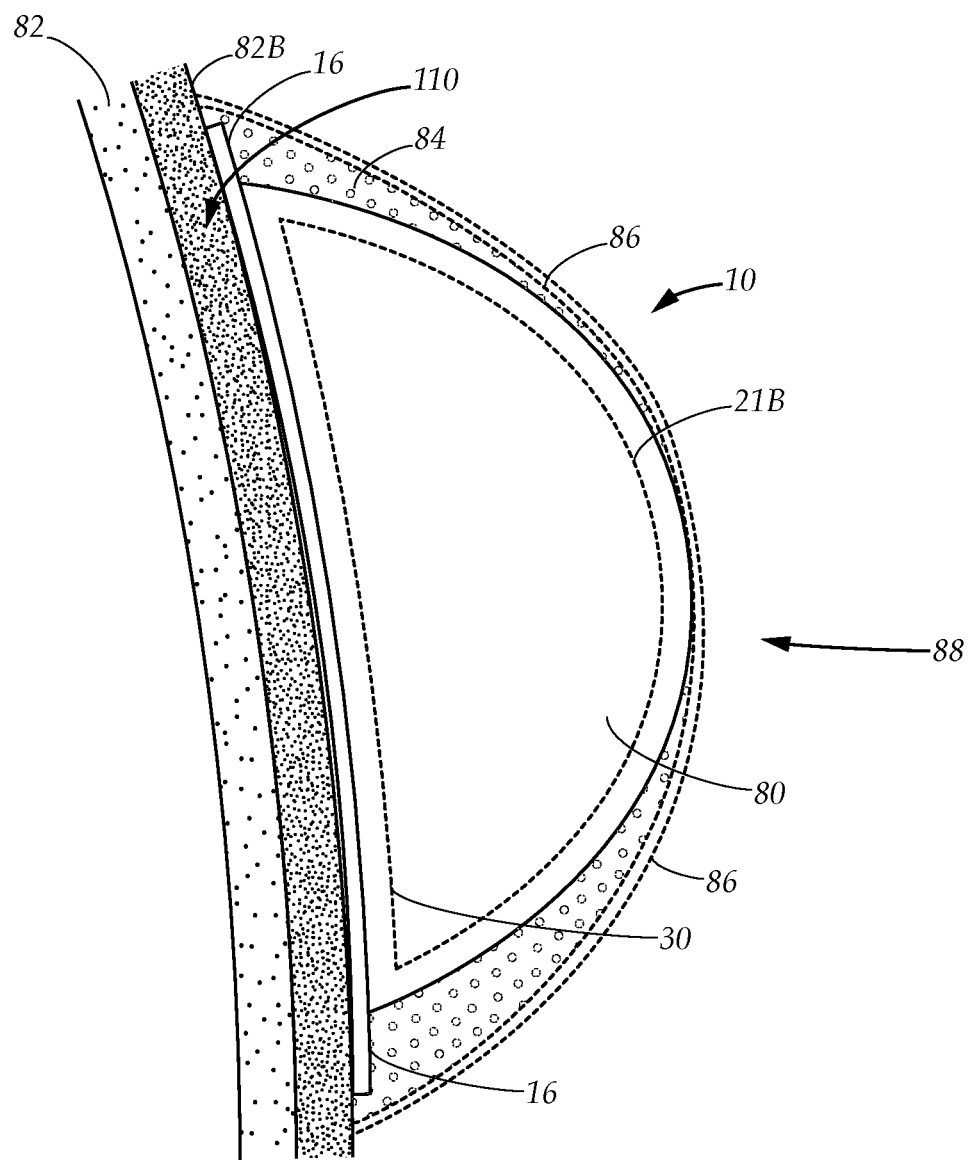
FIG. 14 is a diagrammatic cross section view of the implantable device enveloped within the size adjustable cover positioned at the site of implantation, whereby the implantable device is placed over the chest wall of a patient in a pre-pectoral position, further showing anchoring tabs which are attached to the chest wall to stabilize the implantable device, in accordance with an embodiment in the present disclosure.

FIGS. 1 and 2 illustrate a size adjustable cover 10 adapted to envelop an implantable device 80 used in a surgical application. Turning briefly to FIGS. 3 and 14 while continuing to refer to FIGS. 1 and 2, in a preferred embodiment, the implantable device 80 is a spherical or conical device such as a breast implant or tissue expander employed for augmenting or reconstructing breast tissue 84. Returning to FIGS. 1 and 2 while also referring to FIG. 7, the size adjustable cover 10 comprises a sheet of acellular dermal matrix 12 formed in a two dimensional circular shape having an inner circle 20 and an outer circle 22 which are concentric. The inner circle 20 and the outer circle 22 have an inner circle circumference 20C and an outer circle circumference 22C respectively. The inner circle 20 has an inner circle inner face 21A and an inner circle outer face 21B disposed opposite thereof. The dermal matrix 12 may be synthetic, human or animal derived, or a combination thereof. Furthermore, the dermal matrix 12 may be substituted with any two-dimensional implantable matrix material known to a person of ordinary skill in the art in the field of the invention, which is suitable for reinforcing soft tissue in the surgical application for which the implantable device 80 is to be employed.

The cover 10 further has a plurality of fringes 14 which radiate outwardly from the inner circle circumference 20C. In a preferred embodiment, a plurality of radial cuts 28 divide the dermal matrix 12 from the inner circle circumference 20C and the outer circle circumference 22C to form the fringes 14. The plurality of fringes 14 are arranged circumferentially around the inner circle circumference 20C and collectively form the outer circle 22, and each fringe 14 has a fringe tip 14T which is coextensive with a portion of the outer circle circumference 22C.

Figure 7:
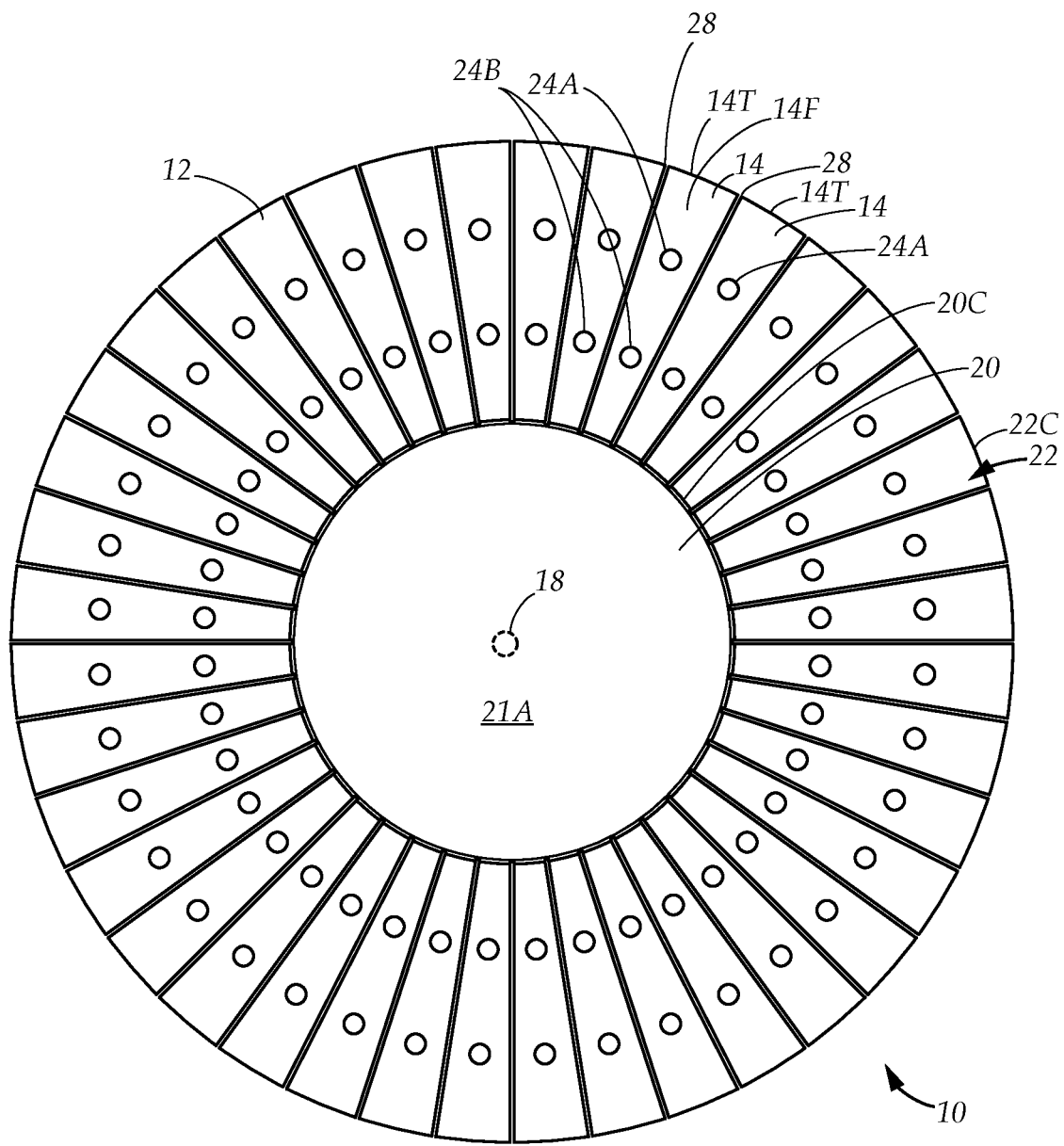
FIG. 7 is a diagrammatic top view of the size adjustable cover lying flat and open, in accordance with an embodiment in the present disclosure.

Referring to FIGS. 2, 3, and 7, the implantable device 80 is positioned upon the cover 10 above the inner circle inner face 21A. The plurality of fringes 14 are folded inwardly towards a center point 18 of the inner circle inner face 21A, and collectively form an overlapping implant pocket 30 which envelops and encases the implantable device 80. The plurality of fringes 14 are linked together by a loop 44 of suture thread 40 which passes through an opening 24B formed in each fringe. Referring to FIGS. 1 and 2, any of the fringes 14 which are not folded inwardly to form the overlapping implant pocket 30 may instead each constitute a stabilization tab 16.

Turning back to FIG. 14, the implantable device 80 enveloped within the cover 10 may then be placed by a surgeon at a site of host implantation 110. In a preferred embodiment, the surgical application is breast surgery and the site of host implantation 110 corresponds to a chest wall 82 of a patient. The cover 10, along with the implantable device 80 enveloped within, is positioned against the chest wall 82, with the overlapping implant pocket 30 facing towards the chest wall 82 and the inner circle outer face 21B facing away from the chest wall 82. The stabilization tabs 16 which radiate outwardly may be attached directly to the chest wall 82 to anchor the cover 10 and the implantable device 80 at a correct implant position. The cover 10 and the implantable device 80 are placed beneath the breast tissue 84 and skin flaps 86.

The use of the cover 10 and the stabilization tabs 16 greatly facilitates revision surgeries by making adjustments of the skin flaps 86 unnecessary. By using the stabilization tabs 16, the surgeon is able to anchor the implantable device 80 directly to the desired position on the chest wall 82 rather than modifying the skin envelope around the implantable device 80 to ensure correct implant position. This approach greatly reduces postoperative pain and opioid use. The invention greatly facilitates breast reconstruction surgeries by allowing the implantable devices 80 to be placed in a pre-pectoral fashion. The cover 10 and the implantable device 80 may be positioned above pectoral muscle 82B located on the chest wall 82, instead of below the pectoral muscle 82B. The use of this technique greatly reduces postoperative pain in the long and short run and will facilitate the avoidance of opioid use in the postoperative setting.

Figure 5:
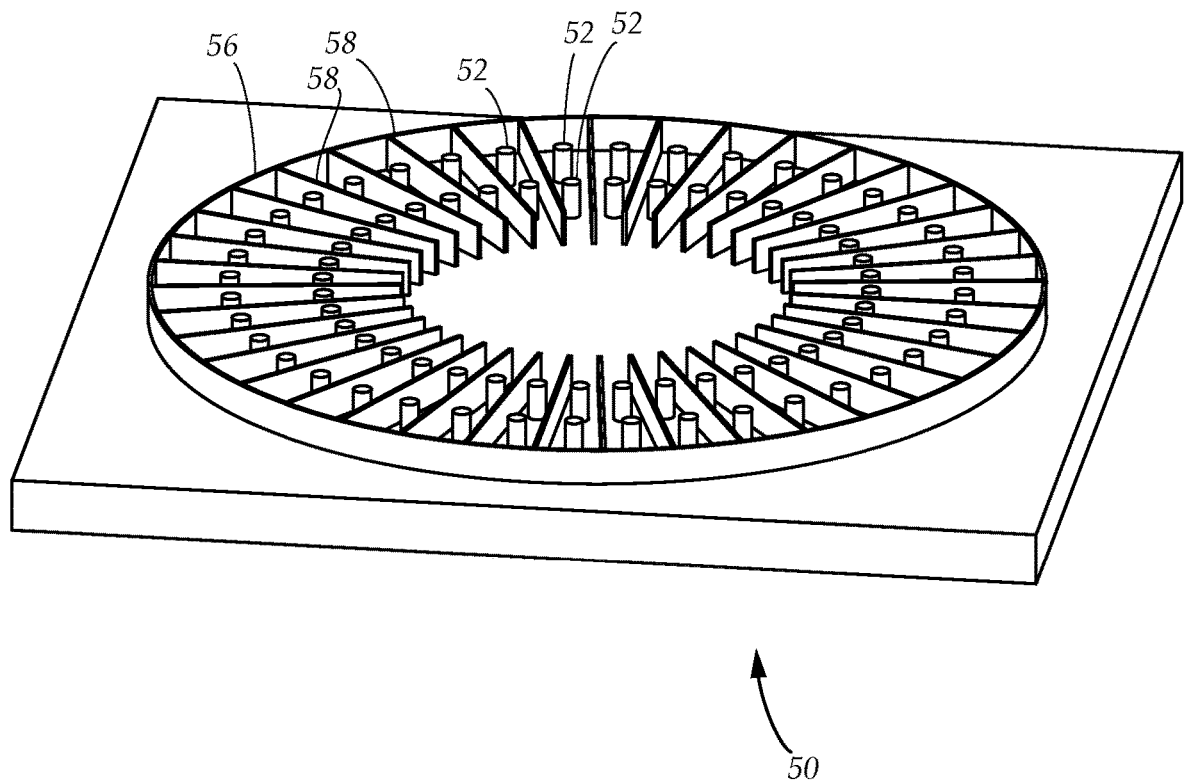
FIG. 5 is a diagrammatic perspective view of a cover die cutter for cutting dermal material to form the size adjustable cover, in accordance with an embodiment in the present disclosure.
Figure 6:
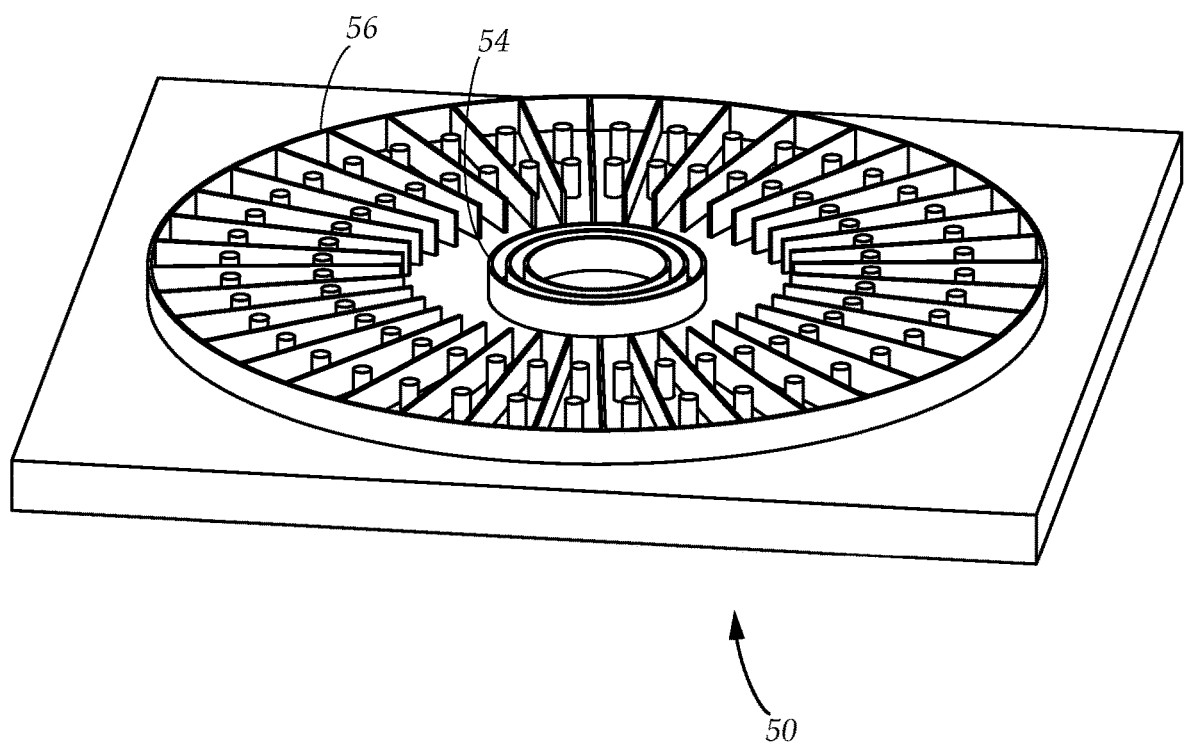
FIG. 6 is a diagrammatic perspective view of the cover die cutter with optional inner circular blades, in accordance with an embodiment in the present disclosure.

Turning now to FIG. 5 while also referring to FIG. 7, the cover 10 is manufactured using a cover die cutter 50 which is used to cut and shape the dermal matrix 12. The use of the cover die cutter 50 allows the cover 10 to be produced in accordance with current FDA and other regulatory approvals, as the dermal matrix 12 differs from existing acellular dermal matrixes only in the use of the cutter 50 to shape the dermal matrix 12 in the patterns described herein. The cover die cutter 50 comprises an outer circular blade 56 adapted to cut the outer circle 22, a plurality of fan shaped blades 58 adapted to create the radial cuts 28 that define the fringes 14, as well as a plurality of hole punches 52 arranged in concentric rows which adapted to perforate the dermal matrix 12 to create the openings 24A and/or inner openings 24B for each fringe 14. In an example embodiment, the openings 24A or inner openings 24B may have a diameter of one millimeter. Referring to FIG. 6 while also referring to FIGS. 5 and 7, the cover die cutter 50 may further comprise one or more inner circular blades 54 which are concentric with the outer circular blade 56. The inner circular blade 54 may be used to score rather than cut the dermal matrix 12 to define the inner circle 20 and the inner circle perimeter 20C. Scoring the inner circle perimeter 20C facilitates the folding of the fringes 14. Furthermore, referring to FIGS. 5-7 along with FIG. 2, the fan shaped blades 58, the inner and outer circular blades 54, 56, and the hole punches 52 may be retractable to allow for variation in the number of fringes 14 and stabilization tabs 16. For example, stabilization tabs 16 may be cut without openings 24A or inner openings 24B. In an example embodiment, the cover 12 may have a diameter of approximately twenty-five centimeters as measured between the outer circle circumference 22C. The inner circle 20 may have a diameter which is approximately one third the diameter of the outer circle 22. Note that the example dimensions provided are not limiting, and the cover 10 may be provided in any size to suit the dimensions of the implantable device 80 and the requirements of the surgical application. Furthermore, the cover die cutter 50 is adapted to cut any alternative implantable matrix material suitable for use in the surgical application, as can be appreciated by a person of ordinary skill in the field of the invention and in adherence with the principles of the present disclosure.

Figure 4:
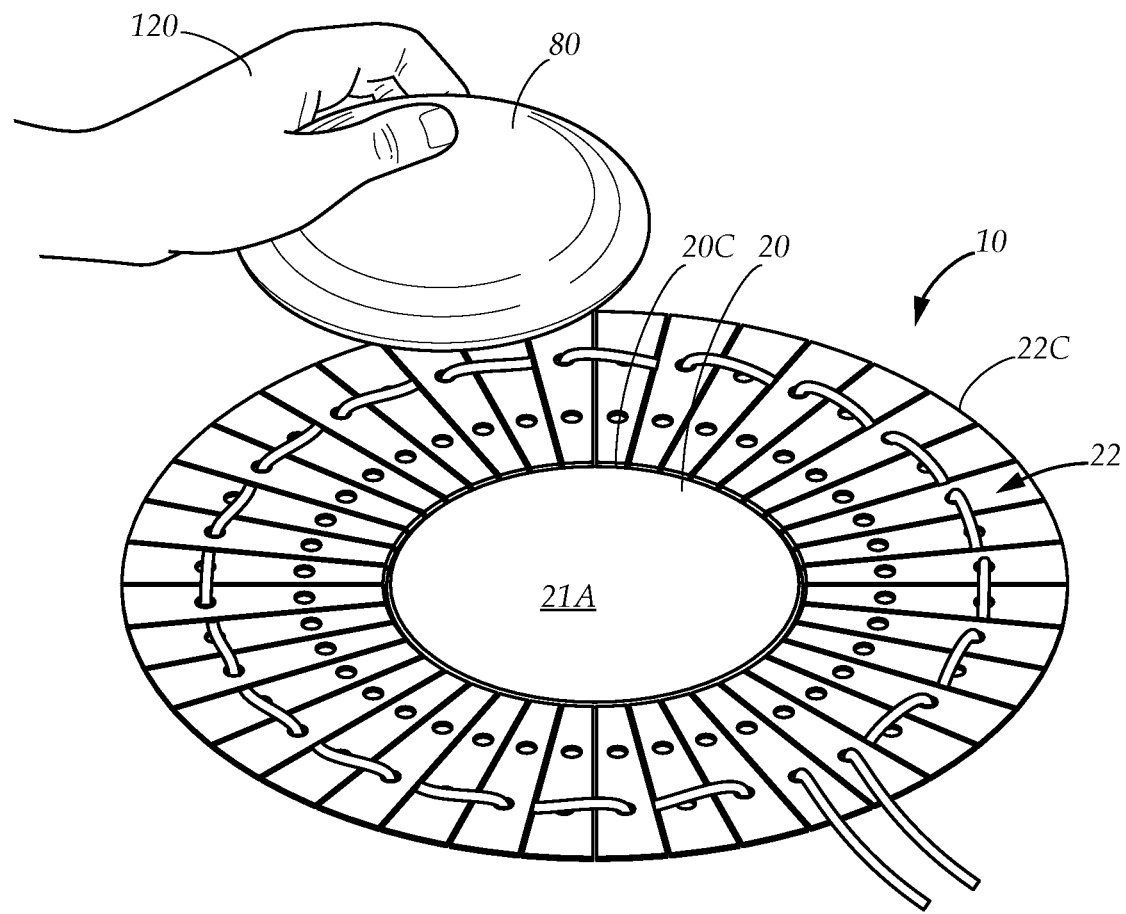
FIG. 4 is a diagrammatic perspective view of the size adjustable cover, depicting openings on each fringe through which a suture thread passes, in accordance with an embodiment in the present disclosure.

Referring to FIGS. 2, 3, and 4 while also referring to FIG. 7, the opening 24A of each fringe is disposed between the fringe tip 14T and the inner circle circumference 20C, while the inner opening 24B is positioned between the opening 24A and the inner circle circumference 20C. Several of the plurality of fringes 14 are linked together by the loop 44 of suture thread 40 passing circularly around the cover 10 and through the opening 24A of each fringe 14 which is used to form the overlapping implant pocket 30. For example, the suture thread 40 may pass through several of the fringes 14 in an alternating sequence whereby every other fringe 14 is excluded from the loop 44. Each excluded fringe 14 may therefore be used as one of the stabilization tabs 16. Note that any number of stabilization tabs 16 may be created by excluding any of the fringes 14 from the loop 44.

Figure 8:
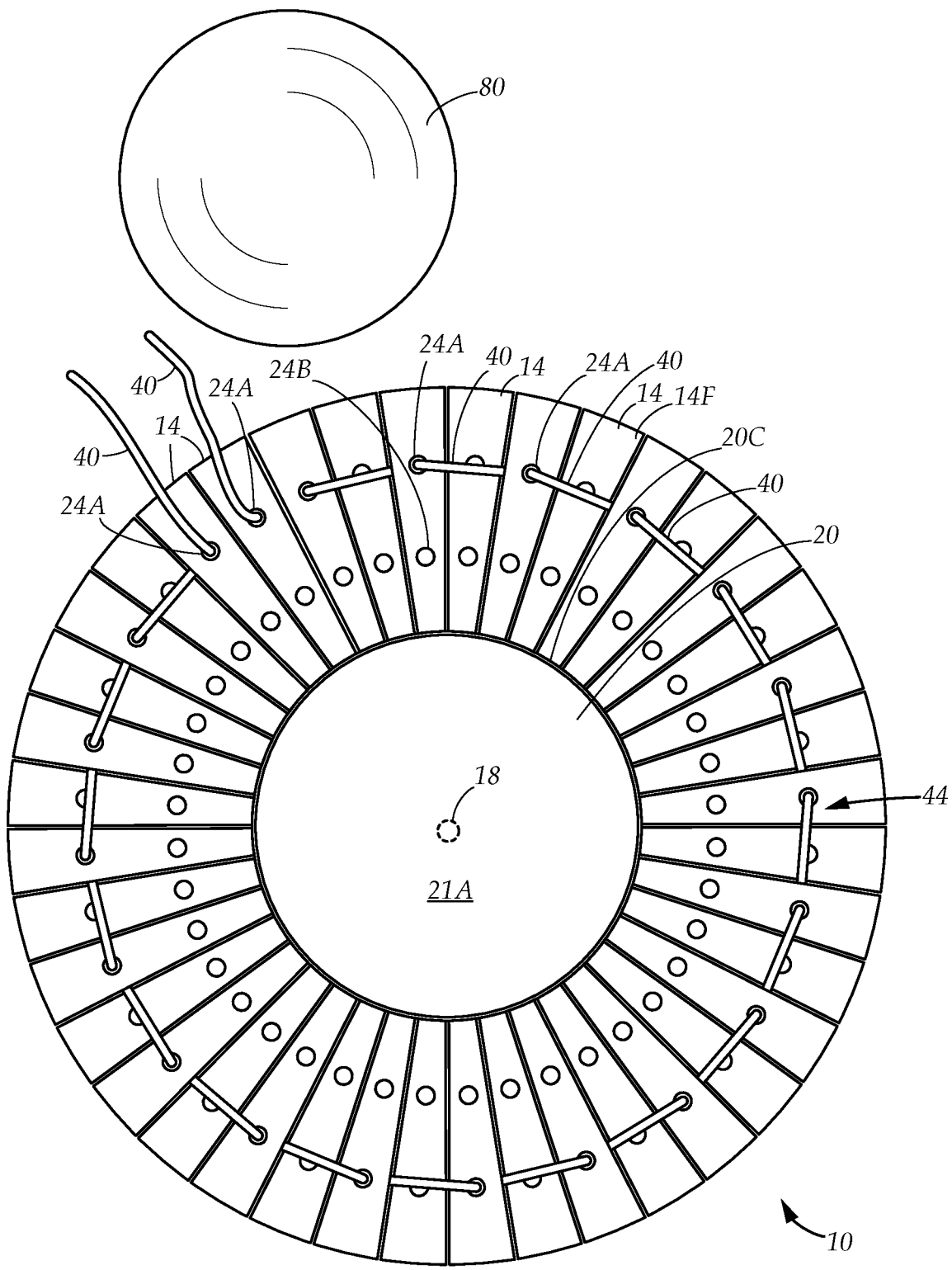
FIG. 8 is a diagrammatic top view of the size adjustable cover, showing the plurality of fringes being linked together by the suture thread passing circularly through the openings of the fringes to form a loop, in accordance with an embodiment in the present disclosure.
Figure 9:
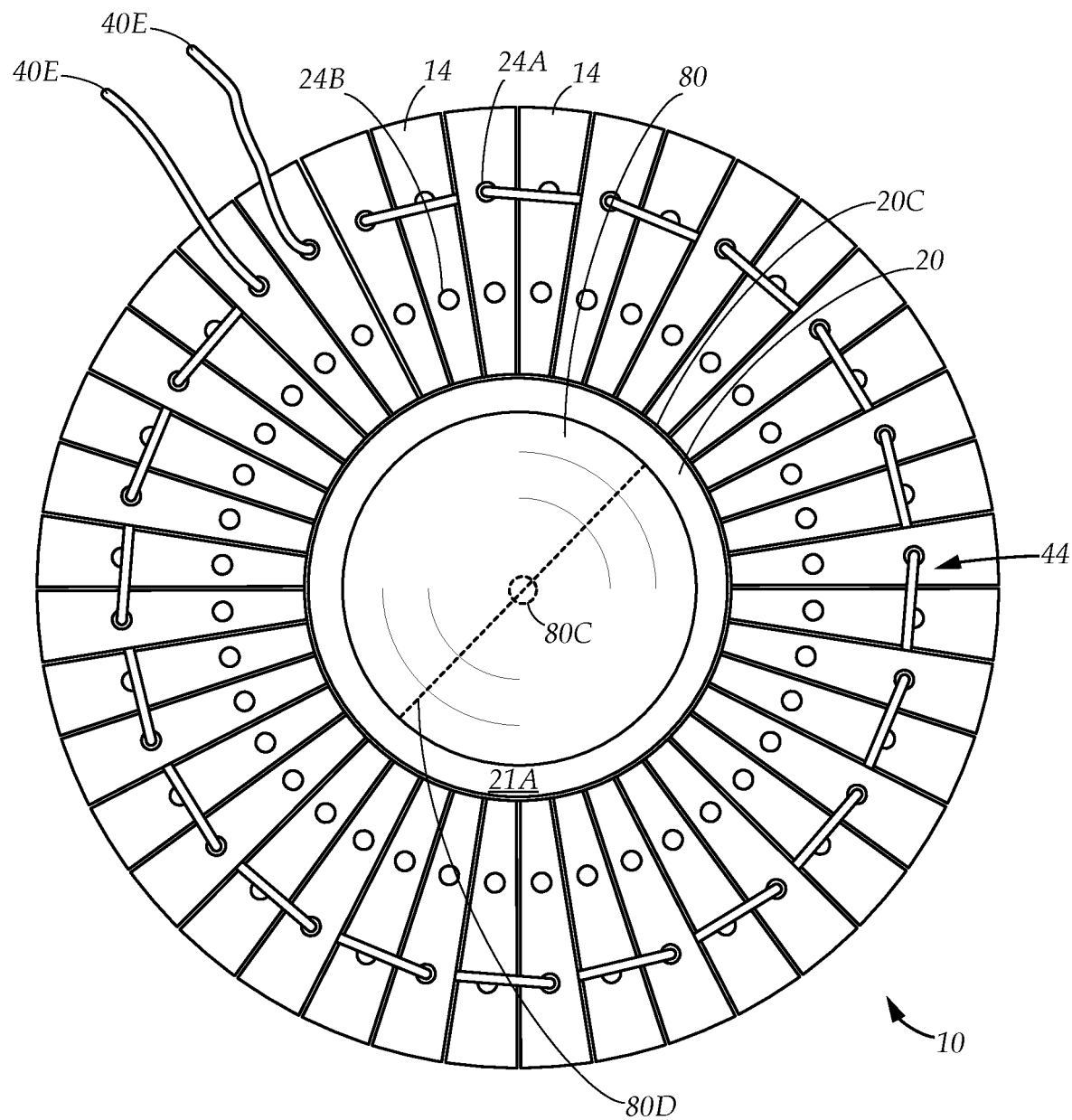
FIG. 9 is a diagrammatic top view showing the implantable device placed upon the inner circle once the plurality of fringes have been linked together, in accordance with an embodiment in the present disclosure.
Figure 10:
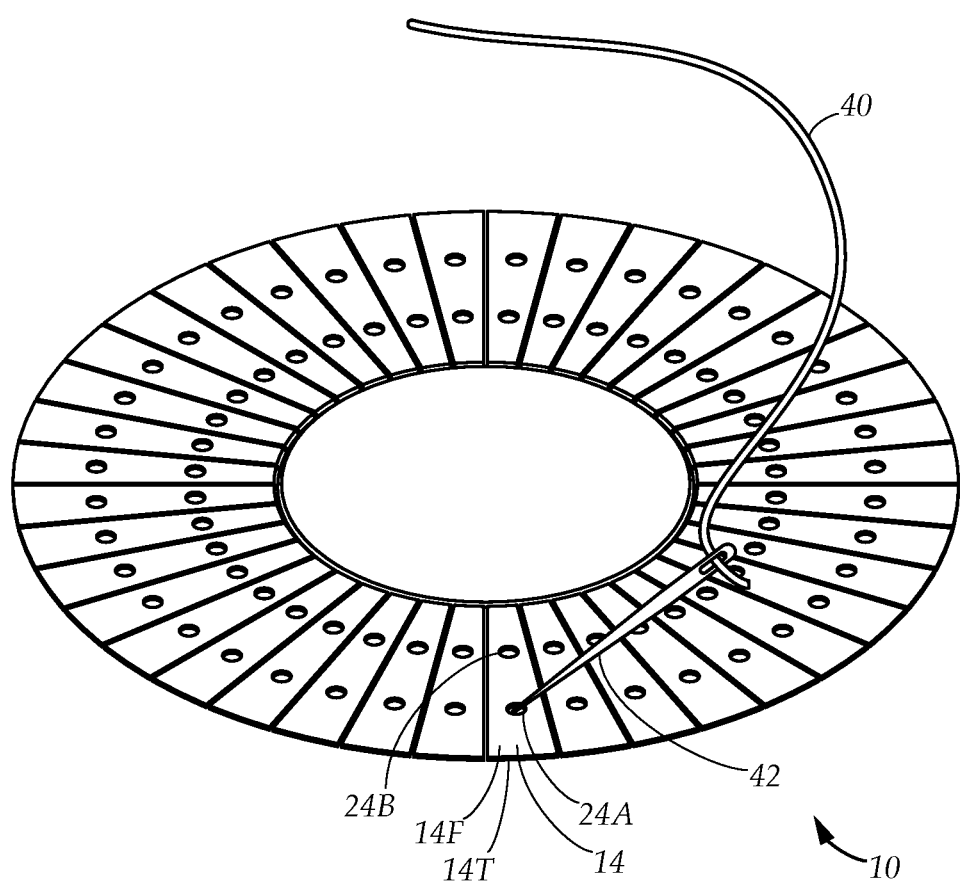
FIG. 10 is a diagrammatic perspective view of the size adjustable cover, showing the suture thread being drawn through the openings using a needle, in accordance with an embodiment in the present disclosure.
Figure 11:
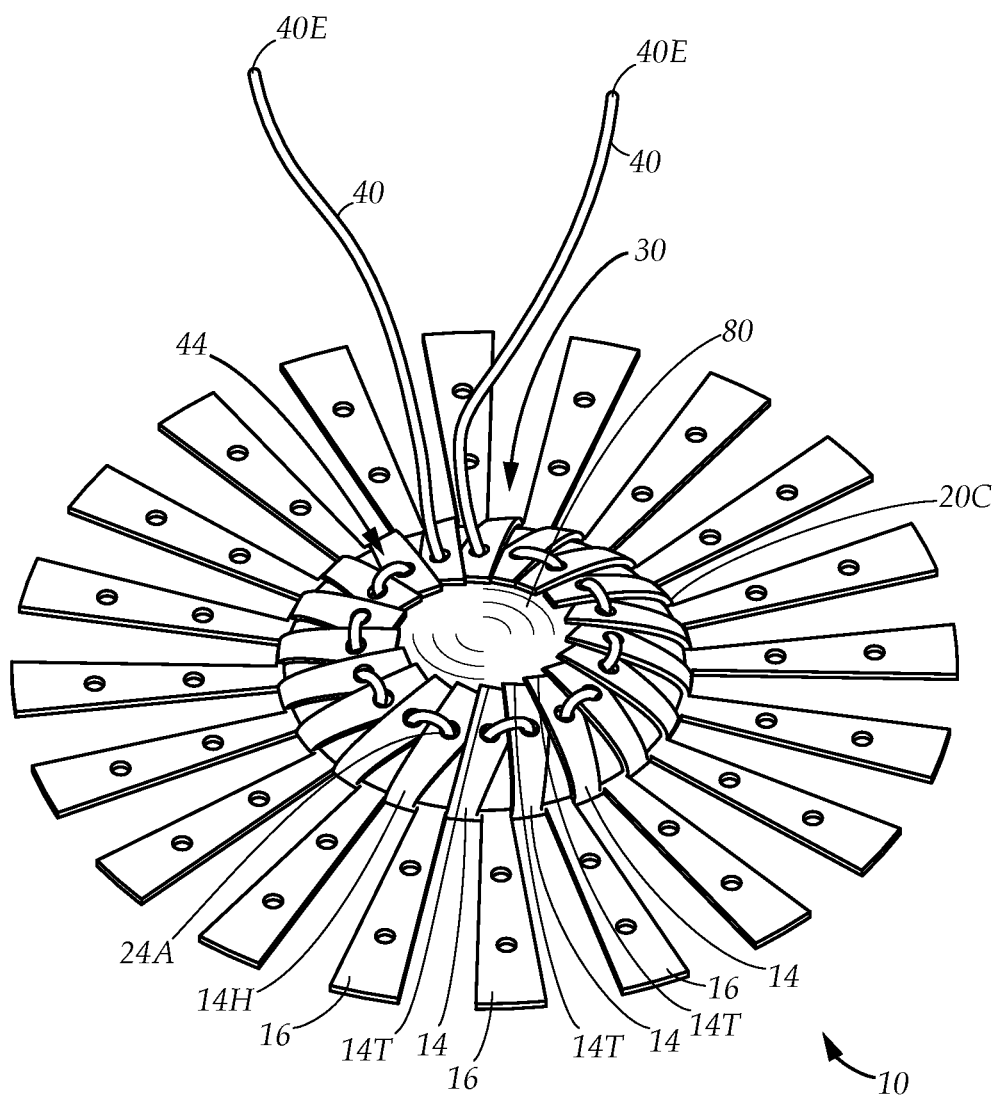
FIG. 11 is a diagrammatic perspective view of the size adjustable cover, showing the loop being tightened in a purse-string fashion to create the overlapping implant pocket which covers the implantable device, in accordance with an embodiment in the present disclosure.

Turning now to FIGS. 7, 8, and 9, when performing the surgical procedure, the cover 10 is unpacked from its sterile package and then soaked in sterile saline solution. The surgeon then selects and places the implantable device 80 upon the inner circle 20, oriented in relation to the center 18 of the inner face 21A. The surgeon then forms the loop 44 by threading the suture thread 40 through the openings 24A of several of the fringes. As shown in FIG. 10, the threading can be performed using a needle 42. Referring to FIGS. 9, 10, and 11, the loop 44 is complete once all the fringes 14 selected to form the overlapping implant pocket 30 are linked together via the suture thread 40. Alternatively, the threading may be performed before the implantable device 80 is placed upon the inner circle 20.

Figure 12:
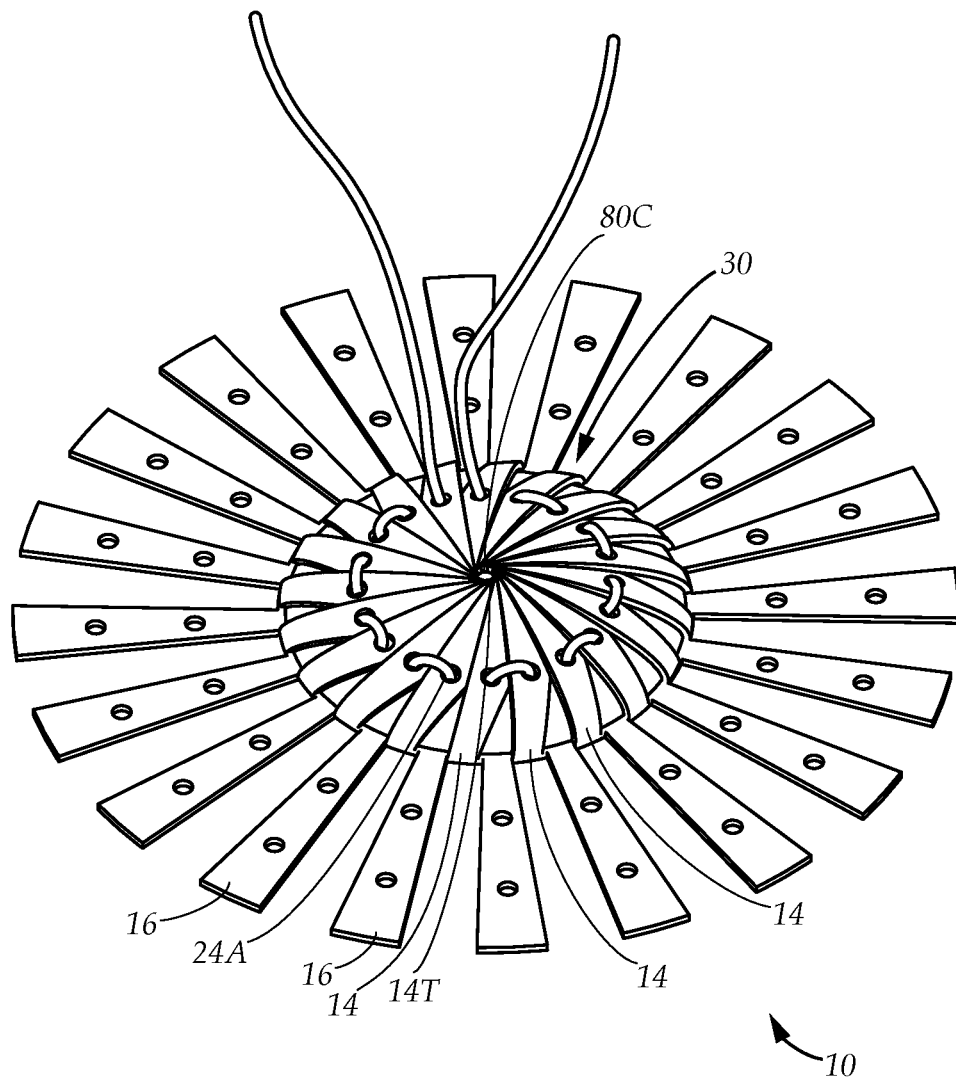
FIG. 12 is a diagrammatic perspective view of the size adjustable cover, showing the overlapping implant pocket formed from fringes having a longer length, in accordance with an embodiment in the present disclosure.

Referring to FIGS. 9, 11, and 12, the fringes 14 or tabs 16 may be trimmed to adjust the size of the overlapping implant pocket 30 to adapt to implantable devices 80 of different dimensions. A circular implantable device 80, such as a breast implant, may have a diameter 80D and a central point 80C. Each fringe 14 may be cut or trimmed between the fringe tip 14T and the inner circle circumference 20C in order to shorten the length of the fringe 14 and create a new fringe tip 14T at the location of the cut. The inner opening 24B is positioned proximate to the inner circle circumference 20C, allowing the fringe 14 to be linked to the suture thread 40 when cut short anywhere between the fringe tip 14T and the inner opening 24B, allowing the overlapping implant pocket 30 to envelop a smaller implantable device 80 with a smaller diameter 80D. Fringes 14 which have not been trimmed (as shown in FIG. 12), allow the overlapping implant pocket 30 to envelop a larger implantable device 80. Referring to FIGS. 9, 10, 11, and 12, the length of the fringes 14 can be adjusted so that the fringe tips 14T of the plurality of fringes 14 meet at the central point 80C of the implantable device 80 when drawn together to form the overlapping implant pocket 30. Note that the loop 44 may be threaded through either the openings 24A or the inner openings 24B depending on the desired length of each fringe 14 as measured from the inner circle circumference 20C to the fringe tip 14T. For example, each fringe 14 may be cut to remove the opening 24A, while leaving the inner opening 24B which is disposed proximate to the inner circle circumference 20C.

Each fringe 14 has a fringe inner face 14F oriented in the same direction as the inner circle inner face 21A, and a fringe outer face 14H positioned opposite thereof. The threading may be performed using a consistent threading pattern by inserting the suture thread 40 through the opening 24A of each fringe 14, passing through the fringe inner face 14F, and then drawing the suture thread 40 away from the fringe outer face 14H. The threading pattern is repeated in either a clockwise or counterclockwise direction circumferentially around the cover 10.

Figure 13:
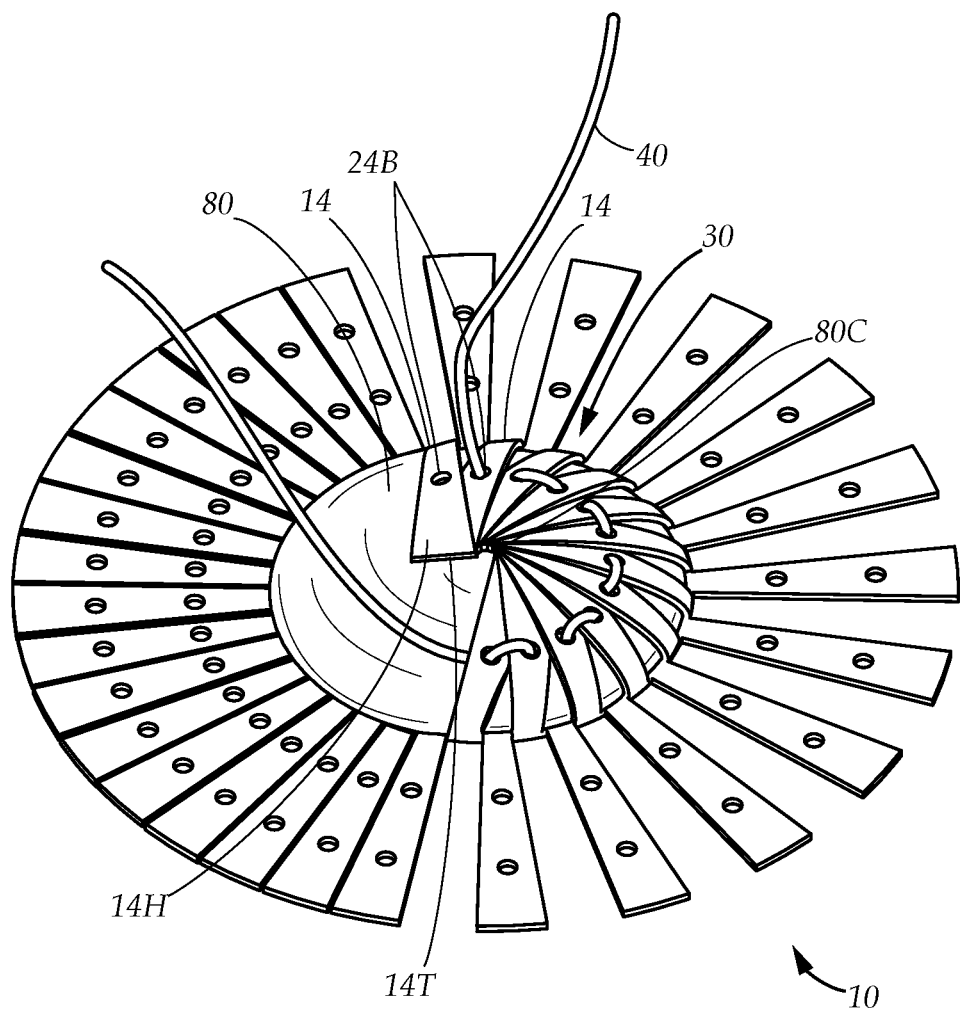
FIG. 13 is a diagrammatic perspective view showing the overlapping arrangement of the fringes which form the overlapping implant pocket, in accordance with an embodiment in the present disclosure.

Referring to FIGS. 9, 11, and 13, the suture thread 40 has two thread ends 40E. To create the overlapping implant pocket 30, the surgeon may pull each thread end 40E to tighten the loop 44 in a purse-string manner and cause the plurality of fringes 14 to fold inwardly towards the inner circle inner face 21A in an overlapping configuration to envelop the implantable device 80. Each fringe 14 folds inwardly about the inner circle circumference 20C, which may be scored to facilitate the folding. The stabilization tabs 16 continue to radiate outwardly from the inner circle circumference 20C. In a preferred embodiment, each fringe 14 is overlapped by the fringe 14 either immediately preceding it or following it in the threading pattern (as shown in FIG. 13). In certain embodiments where the fringes 14 are of sufficient length, the fringe tips 14T of the plurality of fringes 14 are drawn together at the central point 80C of the implantable device 80, thus causing the entirety of the implantable device 80 to be enveloped within the overlapping implant pocket 30. The thread ends 40E may be tied together to secure the loop 44 and prevent the fringes 14 from separating.

Turning now to FIG. 14 while continuing to refer to FIG. 11, once the implantable device 80 is enveloped within the overlapping implant pocket 30, the cover 10 and the implantable device 80 is placed against the chest wall 82 at the site of host implantation 110, with the inner circle outer face 21B facing away from the chest wall 82. In one embodiment, the site of host implantation 110 may be a defect created by a mastectomy and the removal of breast tissue 84. The cover 10 and the implantable device 80 enveloped within may be stabilized by attaching the stabilization tabs 16 to the chest wall 82 using sutures, staples, or other attachment means. As the stabilization tabs 16 are integral with the cover 10, it is unnecessary to suture the tabs to the cover 10, thereby avoiding the possibility of accidentally puncturing the implantable device 80 during stabilization. Any unused or extra stabilization tabs 16 may be trimmed or removed. Once the cover 10 has been secured, the skin flaps 86 may be draped over the cover 10 and the implantable device 80 enveloped within to create a newly reconstructed breast mount 88.

Note that the cover 10 may be employed for implantable devices 80 and surgical applications other than breast reconstruction. For example, the cover 10 may be employed for soft tissue reinforcement, and the stabilization tabs 16 may be used to secure the cover 10 to any site of host implantation 110.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a size adjustable cover for enveloping an implantable device in a surgical application. The disclosure is illustrated by example in the drawing figures, and throughout the written description. It should be understood that numerous variations are possible, while adhering to the inventive concept. Such variations are contemplated as being a part of the present disclosure.

What is claimed is:

1. A size adjustable cover for soft tissue reinforcement, the cover adapted to envelop an implantable device and attach to a site of host implantation upon a patient's body, the cover comprising:
   a flat sheet of implantable matrix having a plurality of fringes projecting radially;
   a plurality of openings, each of the openings passing through one of the fringes; and
   a loop of suture thread passing circularly through the openings, the loop excluding at least two of the fringes and not passing the opening in the at least two of the fringes, said at least two of the fringes thus excluded considered stabilization tabs, the loop adapted to be tightened to form an overlapping implant pocket adapted to envelope the implantable device;

wherein the at least two stabilization tabs are adapted to secure the cover and enveloped implantable device to the site of host implantation.

2. The size adjustable cover as described in claim 1, wherein:
the flat sheet of implantable matrix further comprises an inner circle and an outer circle;
the loop links several of the fringes together in a threading pattern running circumferentially around the inner circle, and the fringes are adapted to fold inwardly in an overlapping configuration whereby each fringe is overlapped by the fringe preceding it in the threading pattern.

3. The size adjustable cover as described in claim 1, wherein:
the flat sheet of implantable matrix further comprises an inner circle and an outer circle, the outer circle and the inner circle each have a circumference, the outer circle divided by a plurality of radial cuts extending between the inner circle circumference and the outer circle circumference, the radial cuts defining the plurality of fringes.

4. The size adjustable cover as described in claim 1, wherein:
each fringe has a fringe inner face, a fringe outer face opposite the fringe inner face, and a fringe tip which projects away from the inner circle, whereby the fringe tips of each fringe of the several fringes are adapted to be drawn together when the loop is tightened to completely envelop the implantable device within the overlapping implant pocket.

5. The size adjustable cover as described in claim 1, wherein:
the suture thread has a pair of thread ends which are adapted to be tied together once the loop is tightened to prevent the fringes from separating.

6. The size adjustable cover as described in claim 1, wherein:
the flat sheet of implantable matrix further comprises an inner circle and an outer circle, each of the inner circle and the outer circle including a circumference;
the implantable device is circular in shape and has a diameter and a central point;
each fringe has a length measured between the inner circle circumference and the fringe tip, and is adapted to be trimmed to shorten the length of the fringe and create a new fringe tip, allowing the cover to adjust to the diameter of the implantable device;
wherein when the loop is tightened, the fringes are pulled, folding inwardly towards the inner circle to form the overlapping implant pocket, whereby the fringe tips of the fringes forming the overlapping implant pocket are adapted to be drawn together at the central point of the implantable device.

7. The size adjustable cover as described in claim 1, wherein:
the implantable device is a breast implant or tissue expander, and the site of host implantation is a chest wall covered by pectoral muscle;
the stabilization tabs are adapted to be secured to the chest wall above the pectoral muscle in a pre-pectoral position to stabilize the implantable device at the site of host implantation and form a reconstructed breast mount.

8. A method for preparing an implantable device configured to be implanted within a patient's body at a site of host implantation, the method comprising the steps of:
providing a circular cover formed of a flat implantable matrix, the cover having an inner circle, and a plurality of fringes projecting radially from the inner circle, the inner circle including an inner circle inner face and an outer circle outer face, each fringe having an opening;
placing the implantable device upon the inner circle;
linking together several of the fringes by threading a suture thread through the opening of each said fringe to create a loop, the loop excluding at least two of the fringes, the at least two excluded fringes considered stabilization tabs;
tightening the loop to fold the fringes inwardly towards the inner circle to form an overlapping implant pocket;
enveloping the implantable device within the overlapping implant pocket; and
attaching the cover and the implantable device to the site of host implantation by securing the stabilization tabs to the site of host implantation.

9. The method as described in claim 8, further comprising:
threading the suture thread through the fringes in a threading pattern running circumferentially around the inner circle; and
forming an overlapping configuration where each fringe is overlapped by the fringe preceding it in the threading pattern.

10. The method as described in claim 8, wherein:
the implantable device is circular in shape and has a diameter and a central point;
each fringe has a fringe tip projecting away from the inner circle; and
the method further comprises drawing together the fringe tips of each of the several fringes at the central point of the implantable device.

11. The method as described in claim 10, wherein:
each fringe has a length measured from the inner circle to the fringe tip; and
the method further comprises adjusting the length of fringe by cutting the fringe between the fringe tip and the opening, and creating a new fringe tip prior to linking together the plurality of fringes.

12. The method as described in claim 8, further comprising:
tying the ends of the suture thread together to prevent the fringes from separating.

13. The method as described in claim 8, wherein:
the implantable device is a breast implant or a tissue expander, and the site of host implantation is a chest wall covered by pectoral muscle; and
the method further comprises attaching the cover and the implantable device to the site of host implantation by positioning the cover such that the inner circle outer face is oriented away from the chest wall, placing the cover upon the chest wall in a pre-pectoral position, and securing the stabilization tabs to the chest wall.

* * * * *